United States Patent
Nellenbach et al.

(10) Patent No.: US 9,510,978 B2
(45) Date of Patent: Dec. 6, 2016

(54) APPLICATOR FOR FEMININE CARE DEVICE

(71) Applicant: The Procter & Gamble Company, Cincinnati, OH (US)

(72) Inventors: Eva Grace Nellenbach, Cincinnati, OH (US); Ayub Ibrahim Khan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 327 days.

(21) Appl. No.: 14/086,126

(22) Filed: Nov. 21, 2013

(65) Prior Publication Data

US 2014/0155808 A1   Jun. 5, 2014

Related U.S. Application Data

(60) Provisional application No. 61/731,529, filed on Nov. 30, 2012.

(51) Int. Cl.
*A61F 13/20* (2006.01)
*A61F 13/26* (2006.01)

(52) U.S. Cl.
CPC .............. *A61F 13/266* (2013.01); *A61F 13/26* (2013.01)

(58) Field of Classification Search
CPC ................................ A61F 13/266; A61F 13/26
See application file for complete search history.

(56) References Cited

U.S. PATENT DOCUMENTS

| | | | |
|---|---|---|---|
| 3,895,634 A * | 7/1975 | Berger | A61F 13/2051 604/14 |
| 5,389,067 A * | 2/1995 | Rejai | A61F 13/26 493/269 |
| 5,792,096 A | 8/1998 | Rentmeester et al. | |
| 6,432,075 B1 | 8/2002 | Wada et al. | |
| 7,104,968 B2 | 9/2006 | Swick | |
| 8,197,434 B2 | 6/2012 | LeMay et al. | |
| 8,444,590 B2 | 5/2013 | LeMay et al. | |
| 2004/0199102 A1* | 10/2004 | LeMay | A61F 13/26 604/11 |
| 2004/0249352 A1 | 12/2004 | Swick | |
| 2010/0016780 A1 | 1/2010 | VanDenBogart et al. | |
| 2011/0066137 A1* | 3/2011 | Parks | A61M 31/00 604/515 |
| 2011/0152742 A1* | 6/2011 | Winkel | A61F 13/266 604/15 |
| 2011/0201992 A1* | 8/2011 | Smet | A61F 13/266 604/11 |

OTHER PUBLICATIONS

PCT International Search Report, mailed Feb. 4, 2014, 39 pages.

* cited by examiner

*Primary Examiner* — Tatyana Zalukaeva
*Assistant Examiner* — Ariana Zimbouski
(74) *Attorney, Agent, or Firm* — Dara M. Kendall; Andrew J. Hagerty

(57) ABSTRACT

Applicators for inserting feminine care devices into the body are provided. The applicators include an applicator barrel having unique insertion tip designs. The insertion tips employ a plurality of petals that can have an inflection or bending point above the bases of the petals.

4 Claims, 4 Drawing Sheets

US 9,510,978 B2

APPLICATOR FOR FEMININE CARE DEVICE

FIELD OF THE INVENTION

The present invention relates to applicators for inserting feminine care devices into the body.

BACKGROUND OF THE INVENTION

Applicators for inserting feminine care devices such as tampons and incontinence devices into the body are well known. Most commercially-available applicators have a plurality of flexible petals on their insertion end that are converged to substantially close the applicator before use. A substantially closed applicator is desired to secure the feminine care device, to maintain the condition of the device such as its cleanliness, and to improve applicator insertion comfort. Once the applicator is inserted into the body, a user can then cause the contained feminine care device to be expelled from the applicator, which includes flexing the petals outwardly to "open" the applicator insertion end to permit the feminine care device to pass through and be expelled from the applicator.

Some applicators are made with the flexible petals in their closed position. Many applicators though are initially made with the flexible petals in an open position to permit a feminine care device to be loaded into the applicator from the insertion end rather than from an opposing gripping end. An example of this type of applicator is shown in FIG. 1, wherein the insertion end of exemplary applicator 10 is illustrated with its plurality of petals 12 in their as-molded or open state. After a feminine care device is loaded into the applicator, the petals are repositioned inwardly through pressure and heat for example. This process can be called post-doming the applicator.

During the post-doming process the insertion petals tend to flex/bend at their respective bases. But this can limit design options for both the petals themselves and the resulting insertion end as defined by the collection of repositioned petals. For example, it may be desirable to include relatively long petal lengths to reduce the amount of force required to open the petals and expel the feminine care device. But an aggressive-appearing insertion end can result as petal lengths increase and flex at their bases during post-doming; that is, the applicator insertion end can become too tapered and "pointy" looking. FIG. 2 illustrates this problem. As shown in FIG. 2, a simplistic forming die 20 can be employed to create a hemispherical-shaped applicator insertion tip, but relatively long petals 22 with a tendency to bend at their bases 24 bend prematurely in the die to result in an aggressively-tapered applicator tip. While the expulsion force associated with the relatively long petals may be a positive, the applicator tip may give the appearance of uncomfortable insertion into the body. The scenario shown in FIG. 2 can also result in petals overlapping at their distal ends, with doming heat and pressure potentially causing the distal ends to become stuck to one another to cause expulsion of the feminine care device undesirably difficult or impossible to expel from the applicator. Embodiments of the present invention can address this and other problems through novel thickness profiles of the applicator insertion tip, the petals and/or surrounding applicator structure.

SUMMARY OF THE INVENTION

Applicators for inserting feminine care devices into the body are described herein. The applicators include an applicator barrel having unique insertion tip designs. The insertion tips employ a plurality of petals that can have an inflection or bending point above bases of the petals. Each of the petals has a petal base defined by the lowest point of a slot between adjacent petals, a petal length extending from the petal base to a petal distal end, and a petal thickness. The insertion tip has a tip length defined from a point 5 mm below the petal bases and extending to the petal distal ends, and an insertion tip wall thickness. In one embodiment, the insertion tip along the tip length comprises a wall thickness angle of greater than or equal to 0.4 degrees. In a second embodiment, the insertion tip thickness varies by at least 15% over a 3 mm section along the tip length. In another embodiment, the insertion tip thickness varies along the tip length via a first taper angle and a second, different taper angle. In yet another embodiment, the petal thickness varies in a non-uniform manner along the petal length. In another embodiment, the petal thickness varies circumferentially along the petal width. These and other embodiments are described in greater detail below.

BRIEF DESCRIPTION OF THE DRAWINGS

The following detailed description of specific embodiments of the present invention can be best understood when read in conjunction with the drawings enclosed herewith.

Figure 1:
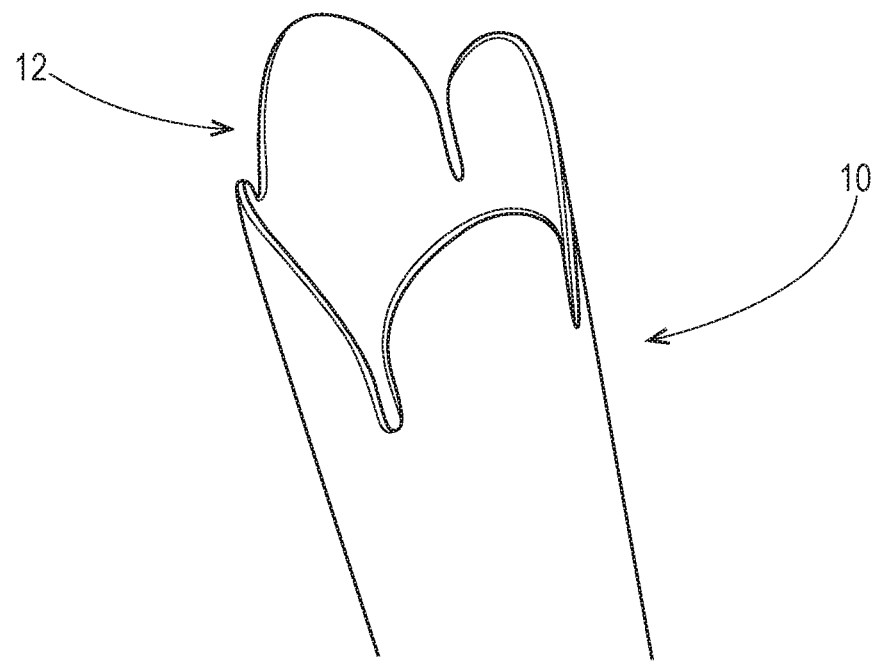
FIG. 1 is a partial perspective view of an applicator barrel.
Figure 2:
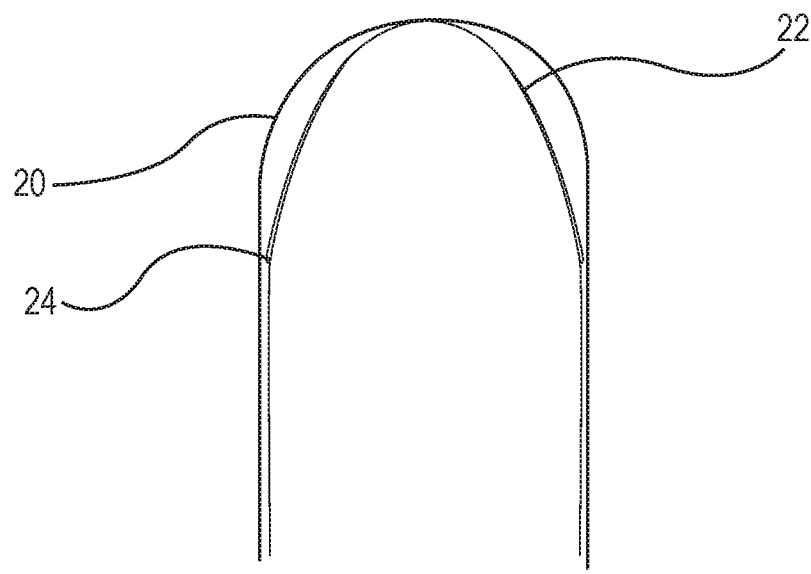
FIG. 2 is a schematic of a post-doming die and applicator insertion tip.

The embodiments set forth in the drawings are illustrative in nature and not intended to be limiting of the invention defined by the claims. Moreover, individual features of the drawings and invention will be more fully apparent and understood in view of the detailed description.

DETAILED DESCRIPTION OF THE INVENTION

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 3:
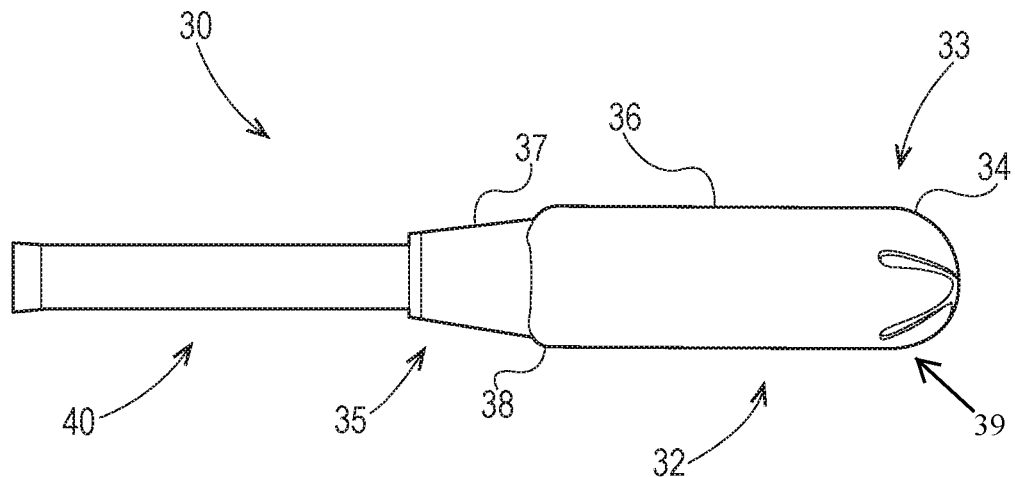
FIG. 3 is a plan view of an applicator comprising a barrel and a plunger.

The present invention generally relates to applicators having improved characteristics. Referring now to the figures, FIG. 3 shows one exemplary embodiment of an applicator 30. The applicator 30 comprises an insertion member or barrel 32 and a plunger 40. Applicator barrel 32 has an insertion tip 34 proximal a first end 33 and an opposing withdrawal end 35. Applicator barrel region 36 is adapted to contain a feminine care device such as, e.g., a tampon or intravaginal incontinence device (e.g., a pessary). Applicator withdrawal end 35 contains a grip region 37 that can, in certain embodiments, be an indentation region. In addition, in certain embodiments, such as, for example, when the grip region 37 is an indentation region, the grip region 37 can be demarcated from the barrel region 36, such as, e.g., by one or more shoulder regions 38. Grip region 37 can comprise three-dimensional surface elements that can protrude outward from the grip region. The present invention is primarily focused on the insertion tip of the applicator, and therefore it is not limited to any particular design features outside of the insertion tip region. Exemplary applicator 30 is a "full-length" applicator. But other types of applicators, including compact applicators, are contemplated by the present invention. Compact applicators generally employ features that permit the plunger part of the applicator to be positioned in a manner that typically shortens the packaged applicator before use. After opening the package, a consumer can then reposition the plunger so that it can be used to expel a feminine care device from the applicator barrel.

Figure 4:
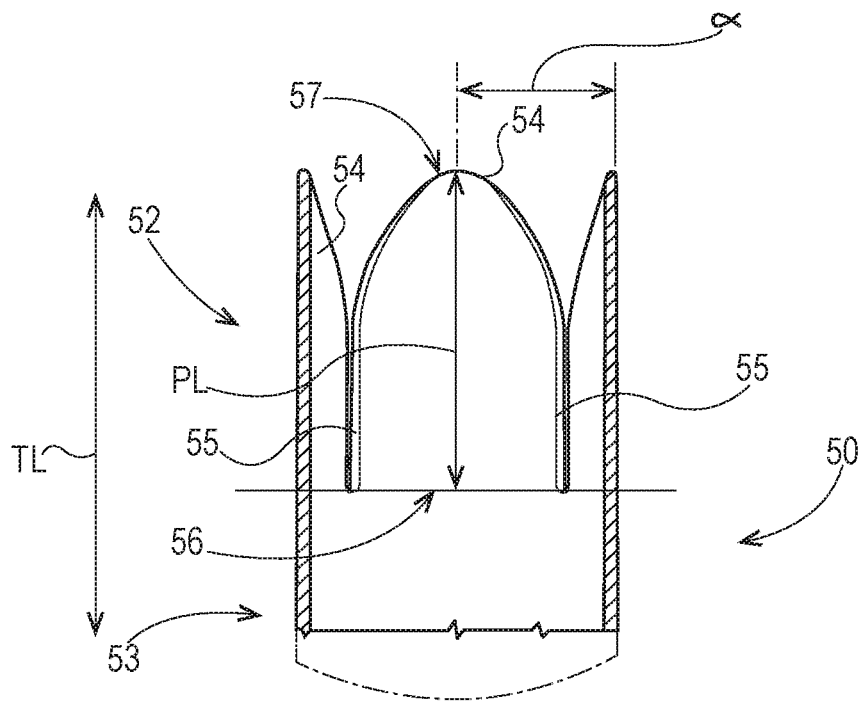
FIG. 4 is a partial cross-sectional view of an applicator insertion tip according to the present invention.

FIG. 4 shows a partial cross-section of an applicator barrel embodiment of the present invention. Applicator barrel 50 includes an insertion tip 52 proximal a first end 53. A plurality of petals 54 is disposed about insertion tip 52. A slot 55 exists between adjacent petals. Each of petals 54 has a petal base 56 and a petal length PL extending from petal base 56 to the petal distal end 57. Insertion tip 52 has a tip length TL defined from a point 5 mm below petal bases 56 and extending to petal distal ends 57.

Insertion tip 52 has a tapering wall thickness along tip length TL defined by angle α. Some commercially-available applicators include a draft angle to aid in removing the applicator from a manufacturing mold, but these angles are generally small; for example, around 0.2 degrees. Embodiments of the present invention include a wall thickness angle α in insertion tip 52 that is at least twice such a draft angle. For example, insertion tip 52 along tip length TL can have a wall thickness angle α of greater than or equal to 0.4 degrees, 0.5 degrees, 0.6 degrees, 0.7 degrees, 0.8 degrees, 1 degree, 2 degrees or more. Other wall thickness angles are contemplated by the present invention, even though they are not explicitly mentioned.

Figure 5:
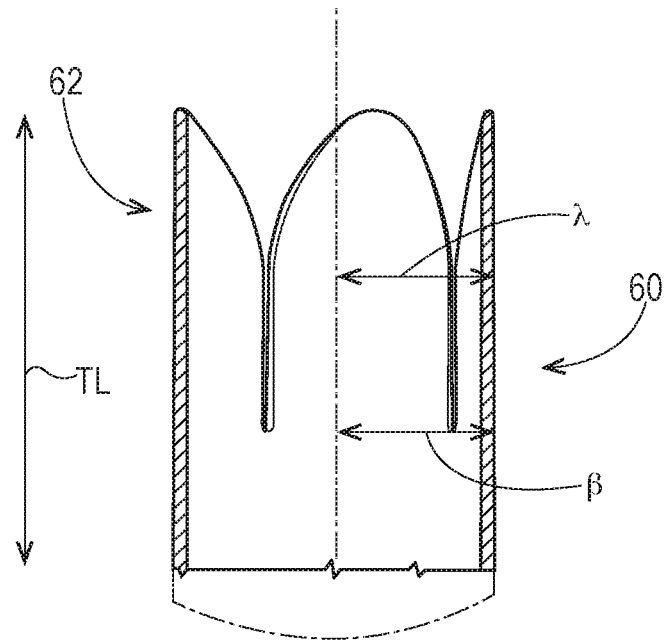
FIG. 5 is a partial cross-sectional view of an applicator insertion tip according to the present invention.

The insertion tip may comprise more than one angle. That is, the insertion tip may have a non-uniform taper along the tip length. For example and with reference to FIG. 5, applicator barrel 60 includes an insertion tip 62 that comprises a first angle β and a second, different angle λ along different sections of tip length TL. The two angles can differ in dimension from one another by 50% or more. In some embodiments, first angle β is less than or equal to 0.3 degrees and second angle λ is greater than or equal to 0.4 degrees.

As noted in the background section, known applicator petals generally bend at the petal bases. Unique design approaches of the present invention permit the creation of one or more inflection or bending points at locations other than the petal bases (see, e.g., inflection or bending point 39 in FIG. 3). The design approaches provided by the present invention reduce and/or increase flexural resistance in targeted regions of the insertion tip. In one embodiment, the wall thickness of the insertion tip varies by at least 15%, 20%, or 25% over a 3 mm, 4 mm, or 5 mm section along the tip length to create a petal doming inflection point. This creates a step change in wall thickness. A thickness step change can be imparted via a single wall thickness angle with surrounding sections being devoid of a wall thickness taper, or via two or more angles as described above in connection with FIG. 5. Petal inflection points of the present invention can exist proximal the petal bases. In other embodiments, petal inflection points can exist above the petal bases; for example, at least 1 mm, at least 2 mm, or at least 3 mm above the petal bases.

Figure 6:
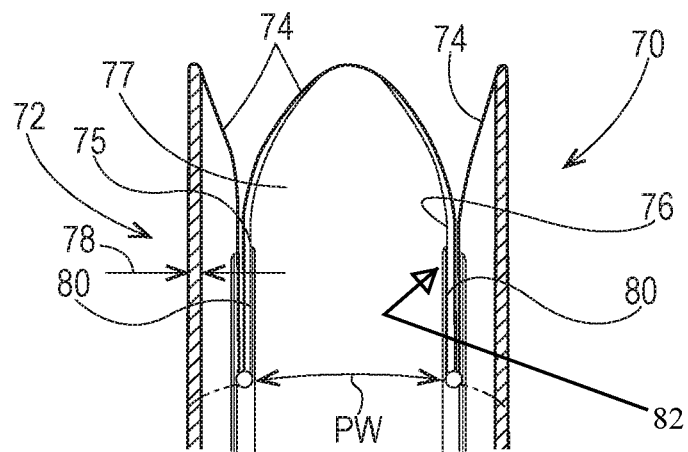
FIG. 6 is a partial cross-sectional view of an applicator insertion tip according to the present invention.

Petal wall thickness can also vary circumferentially along the width of the petals. One exemplary technique includes employing vertical ribs at one or more locations across the width of the petals. Referring now to FIG. 6, applicator barrel 70 includes an insertion tip 72 with a plurality of petals 74. Each of petals 74 includes opposing first and second edges 75/76, a petal width PW extending circumferentially from first edge 75 to second edge 76, and inner surface 77, and petal thickness 78. Ribs 80 extend along a portion of the first and second edges 75/76 of petals 74. The petal inflection or bending point 82 will occur at the distal ends of ribs 80. As can be seen in FIG. 6, ribs 80 can extend longitudinally beyond the petal bases. One of ordinary skill in the art should appreciate that the number, location, and geometrical features of the ribs can vary from that shown in FIG. 6.

Figure 7:
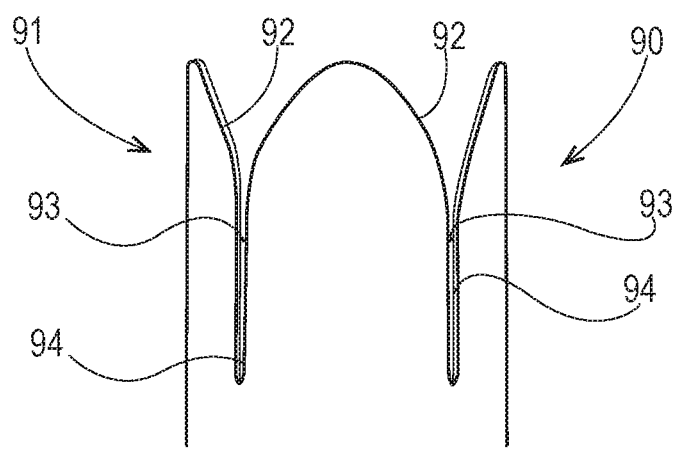
FIG. 7 is a partial plan view of an applicator insertion tip according to the present invention.

Another embodiment of the present invention, with reference to FIG. 7, includes employing material into a portion of the slots that exist between adjacent petals. Applicator barrel 90 includes an insertion tip 91 having a plurality of petals 92 with slots 93 between adjacent petals. As shown in FIG. 7, a portion of slots 93 include material 94. The bridging material 94 will preferably only extend along a portion of the petal length PL. Bridging material 94 will generally only extend a portion of the petal thickness as can be seen in FIG. 7. The bridging material can be the same or different from the material used to manufacture the surrounding applicator features.

The applicator barrel and plunger can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, poly hydroxyalkanoate, ethylene vinyl acetate, polyurethane, silicone, derivatives thereof, copolymers thereof, mixtures thereof, or any suitable smooth plastic material. Examples of suitable materials are disclosed in, e.g., U.S. Pat. Nos. 5,346,468 and 5,558,631. In certain embodiments, additives can be included in the material to alter or enhance certain material properties. Suitable additives include, for example, mold release agents, slip agents, surface energy modifiers, pearlescent agents, and/or any other suitable additives. In certain embodiments, the applicator barrel can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the applicator components can include a textured surface. Texture can be provided in any suitable manner, such as, e.g., by designing texture into or adding texture to the applicator components. For example, a rubbery material such as thermoplastic elastomer can be included in the gripping region of the applicator barrel.

Applicator components can be made by a number of different techniques, including, for example, by injection molding, blow molding, spirally winding layers of material, and convolutedly winding one or more layers. Applicators of the present invention are preferably made from a thermoplastic polymer material and are injection molded. The applicator barrels are preferably molded with the petals in an open position and then post-domed using additional equipment and processes (e.g., urging the applicator insertion tip into a heated doming die). It should be appreciated however that the insertion tip and petal features described herein can be applied to applicators that are formed with the petals in a closed configuration.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An applicator for inserting feminine care devices into the body, the applicator comprising:
    a. a barrel comprising an insertion tip proximal a first end;
    b. a plurality of spaced apart petals disposed about the insertion tip, each of the petals including a petal base, a petal distal end, a petal length between the petal base and the petal distal end, and a petal thickness;
    c. wherein the petal thickness varies in a non-uniform manner along the petal length via a petal thickness step change comprising two or more wall thickness taper angles.

2. The applicator of claim 1, wherein the two or more wall thickness taper angles comprise a first wall thickness taper angle and a second wall thickness taper angle, and wherein the first wall thickness taper angle is less than or equal to 0.3 degrees.

3. The applicator of claim 2, wherein the second wall thickness taper angle is greater than or equal to 0.4 degrees.

4. The applicator of claim 1, wherein the two or more wall thickness taper angles comprise a first wall thickness taper angle and a second wall thickness taper angle, and wherein the second wall thickness taper angle is greater than the first wall thickness taper angle by at least 50%.

* * * * *